(12) United States Patent
Ahn et al.

(10) Patent No.: US 11,559,248 B2
(45) Date of Patent: Jan. 24, 2023

(54) REAL-TIME PARATHYROID SENSING SYSTEM

(71) Applicants: PUKYONG NATIONAL UNIVERSITY INDUSTRYUNIVERSITY COOPERATION FOUNDATION, Busan (KR); UNIST (ULSAN NATIONAL INSTITUTE OF SCIENCE AND TECHNOLOGY), Ulsan (KR)

(72) Inventors: Yeh-Chan Ahn, Busan (KR); Sung Chul Bae, Ulsan (KR)

(73) Assignees: PUKYONG NATIONAL UNIVERSITY INDUSTRYUNIVERSITY COOPERATION FOUNDATION, Busan (KR); UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 344 days.

(21) Appl. No.: 16/764,488

(22) PCT Filed: Nov. 5, 2018

(86) PCT No.: PCT/KR2018/013286
§ 371 (c)(1),
(2) Date: May 15, 2020

(87) PCT Pub. No.: WO2019/098580
PCT Pub. Date: May 23, 2019

(65) Prior Publication Data
US 2020/0359956 A1 Nov. 19, 2020

(30) Foreign Application Priority Data
Nov. 17, 2017 (KR) .......................... 10-2017-0154274

(51) Int. Cl.
A61B 5/00 (2006.01)

(52) U.S. Cl.
CPC .......... *A61B 5/4227* (2013.01); *A61B 5/0059* (2013.01); *A61B 5/0071* (2013.01);
(Continued)

(58) Field of Classification Search
CPC ................ A61B 5/0059; A61B 5/0071; A61B 5/0077; A61B 5/0082; A61B 5/4227; A61B 5/4887; A61B 5/7228; A61B 5/746
See application file for complete search history.

(56) References Cited

U.S. PATENT DOCUMENTS

| 2012/0010483 A1* | 1/2012 | Mahadevan-Jansen ..................... A61B 5/4227 600/310 |
| 2013/0274596 A1 | 10/2013 | Azizian et al. |

(Continued)

FOREIGN PATENT DOCUMENTS

| JP | 2016087062 A | 5/2016 |
| JP | 5958922 B2 | 8/2016 |

(Continued)

OTHER PUBLICATIONS

Korean Patent Abstract (in English) of Korean Patent App. Pub. No. KR10-2014-0101930 A, Pub. Date Aug. 21, 2014, downloaded from https://worldwide.espacenet.com.
(Continued)

*Primary Examiner* — Mark D Remaly
(74) *Attorney, Agent, or Firm* — Barcelo, Harrison & Walker, LLP (57) ABSTRACT

The present invention relates to a parathyroid sensing system, and includes: a modulator for generating a modulation signal having a predetermined frequency; a lock-in amplifier and a light source which receive information on the modu-
(Continued)

lation signal; an excitation filter for transmitting, among light emitted from the light source, only excitation light that excites parathyroid glands; an emission filter connected to a probe and selectively transmitting only fluorescence emitted from the parathyroid glands; a near-infrared sensor for sensing the autofluorescence that has passed through the emission filter, and converting the sensed autofluorescence into an electric signal; and a speaker for generating an alarm through the electric signal. Through the present invention, the locations of the parathyroid glands may be precisely identified even when lights are turned on in an operating room, and convenience may be provided by alerting a surgeon by means of an alarm when the parathyroid glands are detected. In addition, the locations of the parathyroid glands may be precisely detected, even when the probe is not directly in contact with the parathyroid glands, by using the autofluorescence characteristics of the parathyroid glands.

6 Claims, 6 Drawing Sheets

(52) U.S. Cl.
CPC .......... *A61B 5/0077* (2013.01); *A61B 5/0082* (2013.01); *A61B 5/4887* (2013.01); *A61B 5/7228* (2013.01); *A61B 5/746* (2013.01)

(56) References Cited

U.S. PATENT DOCUMENTS

| | | | |
|---|---|---|---|
| 2014/0309527 A1 | 10/2014 | Namati et al. | |
| 2015/0182118 A1 | 7/2015 | Bradbury et al. | |
| 2016/0073949 A1* | 3/2016 | Grant | A61B 5/1032 600/407 |
| 2017/0105623 A1 | 4/2017 | Mahadevan-Jansen et al. | |
| 2017/0236022 A1 | 8/2017 | Abbas et al. | |

FOREIGN PATENT DOCUMENTS

| | | |
|---|---|---|
| KR | 1020120063342 A | 6/2012 |
| KR | 10-2014-0101930 A | 8/2014 |
| KR | 1020170017937 A | 2/2017 |

OTHER PUBLICATIONS

Notice of Allowance (In Korean), dated Apr. 13, 2018, of Priority Application No. KR10-2017-0154274, filing date Nov. 17, 2017.
European Search Report (in English), dated Jun. 28, 2021, of European Patent Application No. EP 18 87 8491.2, EP National Stage of International Application PCT/KR2018/013286, filing date Nov. 5, 2018.
Document title "Developing a Clinical Prototype to Guide Surgeons for intraoperative Label-Free identification of Parathyroid Glands in Real Time", name of applicants of cited document: Giju Thomas, Ph.D et al., (Vanderbilt Biophotonics Center, Vanderbilt University), presented at the 3rd World Congress on Thyroid Cancer, held from Jul. 27-30, 2017, in Boston, MA US., article published at https://www.researchgate.net.
Korean Patent Abstract (in English) of Korean Patent App. Pub. No. KR10-2012-0063342 A, Pub. Date Jun. 15, 2012, downloaded Jan. 26, 2021, from https://worldwide.espacenet.com.
Korean Patent Abstract (in Korean) of Korean Patent App. Pub. No. KR10-2017-0017937 A, Pub. Date Feb. 15, 2017, downloaded Jan. 26, 2021, from https://worldwide.espacenet.com.
Japanese Patent Abstract (in English), of Japan Patent App. Pub. No. JP 5958922 B2, Pub. Date Aug. 2, 2016, downloaded Jan. 26, 2021, from https://worldwide.espacenet.com.
Japanese Patent Abstract (in English), of Japan Patent App. Pub. No. JP 2016-087062 A, Pub. Date May 23, 2016, downloaded Jan. 26, 2021, from https://worldwide.espacenet.com.

* cited by examiner

REAL-TIME PARATHYROID SENSING SYSTEM

CROSS-REFERENCE TO RELATED APPLICATIONS

This application is the national stage of International Patent Cooperation Treaty Application PCT/KR2018/013286 filed 5 Nov. 2018, which claims priority from Korean Patent Application No. 10-2017-0154274 filed 17 Nov. 2017, in the Korean Intellectual Property Office. The entire contents of said applications are incorporated herein by reference for all purposes.

BACKGROUND

Technical Field

The present invention relates to a real-time parathyroid sensing system, and more particularly, to a sensing system that may determine a location of parathyroid by sensing autofluorescence of the parathyroid.

Background Art

In thyroid dissection for removing thyroid tumors, it is very important to preserve parathyroid for maintaining calcium homeostasis of our body. Since the parathyroid is a very small and delicate organ having a weight of 35 to 45 mg and a size of approximately 5×3×1 mm, it is not easy to distinguish the parathyroid from surrounding tissues such as the thyroid and a lymph gland with the naked eyes.

Figure 1:
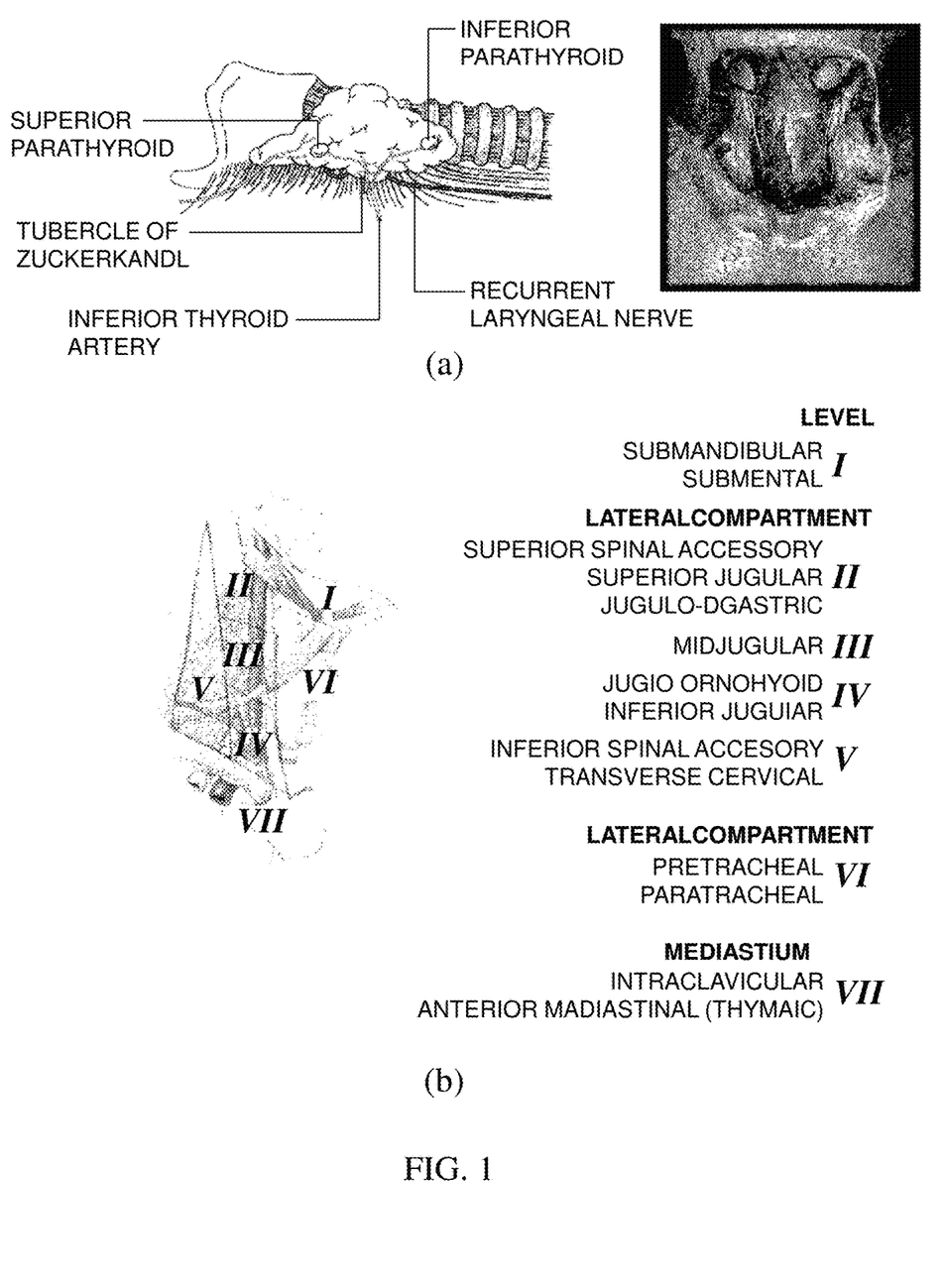
FIG. 1(a) illustrates a location of parathyroid and FIG. 1(b) illustrates subgroups of lymph nodes.

FIG. 1(a) illustrates a location of parathyroid and FIG. 1(b) illustrates lymph node subgroups of the neck separated into levels relevant for surgical dissections.

Referring to FIG. 1(a), it can be seen that the parathyroid is positioned at a rear side of thyroid positioned at the center of a front of a neck. There are generally a total of 4 parathyroids, and one is positioned at each of left upper and lower portions and one is positioned at each of right upper and lower portions.

As indicated in FIG. 1(b) illustrating the subgroups of the lymph gland, lymph glands (level VI) surrounding thyroid are dissected together by considering a metastasis possibility at the time of thyroid tumor dissection. This is referred to as central compartment neck dissection (CCND). Dividing the lymph gland into the subgroups according the location is referred to as a level system. The level system is classified into a total of 7 levels. It is characterized in that among 7 levels, the thyroid is present in section level VI and papillary thyroid carcinoma primarily spreads well to lymph gland level VI.

At the time of performing the central compartment neck dissection, since a normal lymph gland is very small, it is almost impossible to identify the normal lymph gland with the naked eyes. Accordingly, both a fatty tissue and a connective tissue including the lymph gland are removed at the time of dissecting the lymph gland.

Here, it becomes important to determine the location of the parathyroid. The reason is that it is not easy to distinguish the parathyroid from the surrounding fatty tissue or connective tissue in section level VI unless a person is a skilled surgeon.

At present, a medical device has been commercialized, which allows the surgeon to determine the location of a nerve by using electrical conduction of the nerve in order to preserve a vocal nerve at the time of surgery of the thyroid tumors, but development of a device which can minutely determine the location of the parathyroid is insufficient.

DISCLOSURE

Technical Problem

An object of the present invention is to provide a sensing system that sounds an alarm when a probe or a surgical instrument accesses parathyroid by using a point that the parathyroid emits stronger autofluorescence than thyroid and surrounding tissues.

Technical Solution

In order to solve the technical problem, a parathyroid sensing system according to the present invention includes: a modulator for generating a modulation signal having a predetermined frequency; a lock-in amplifier and a light source which receive information on the modulation signal; an excitation filter for transmitting, among light emitted from the light source, only excitation light that excites parathyroid glands; an emission filter connected to a probe and selectively transmitting only autofluorescence emitting from the parathyroid glands; a near-infrared sensor for sensing the autofluorescence that has passed through the emission filter, and converting the sensed autofluorescence into an electric signal; and a speaker for generating an alarm through the electric signal.

In addition, the light source includes a controller modulating an intensity of the light source based on the received modulation signal information.

In addition, the near-infrared sensor is a photomultiplier tube (PMT) or avalanche photo diode (APD).

Further, the lock-in amplifier receives the electric signal from the near-infrared sensor and generates a signal without noise based on the modulation signal information received from the modulator.

Further, the parathyroid sensing system further includes a micro-controller converting the electric signal into an electric signal which may be recognized by the speaker.

Further, the emission filter is connected to a first optical fiber and the excitation filter is connected to a second optical fiber and both are integrated in one probe.

Advantageous Effects

Effects of a real-time parathyroid sensing system according to embodiments of the present invention will be described below.

Through the present invention, a location of parathyroid can be precisely determined even while an operating room is lighted.

Further, the locations of the parathyroid glands can be precisely detected, even when the probe is not directly in contact with the parathyroid glands, by using the autofluorescence characteristics of the parathyroid glands.

Further, convenience can be provided by alerting a surgeon by means of an alarm when the parathyroid glands are detected.

However, effects obtainable by a real-time parathyroid sensing system according to embodiments of the present invention are not limited to the aforementioned effects and other unmentioned effects will be clearly understood by those skilled in the art from the following description.

BRIEF DESCRIPTION OF THE DRAWINGS

In order to help understand the present invention, the accompanying drawings which are included as a part of the Detailed Description provide embodiments of the present invention and describe the technical spirit of the present invention together with the Detailed Description.

DETAILED DESCRIPTION

Best Mode

Figure 2:
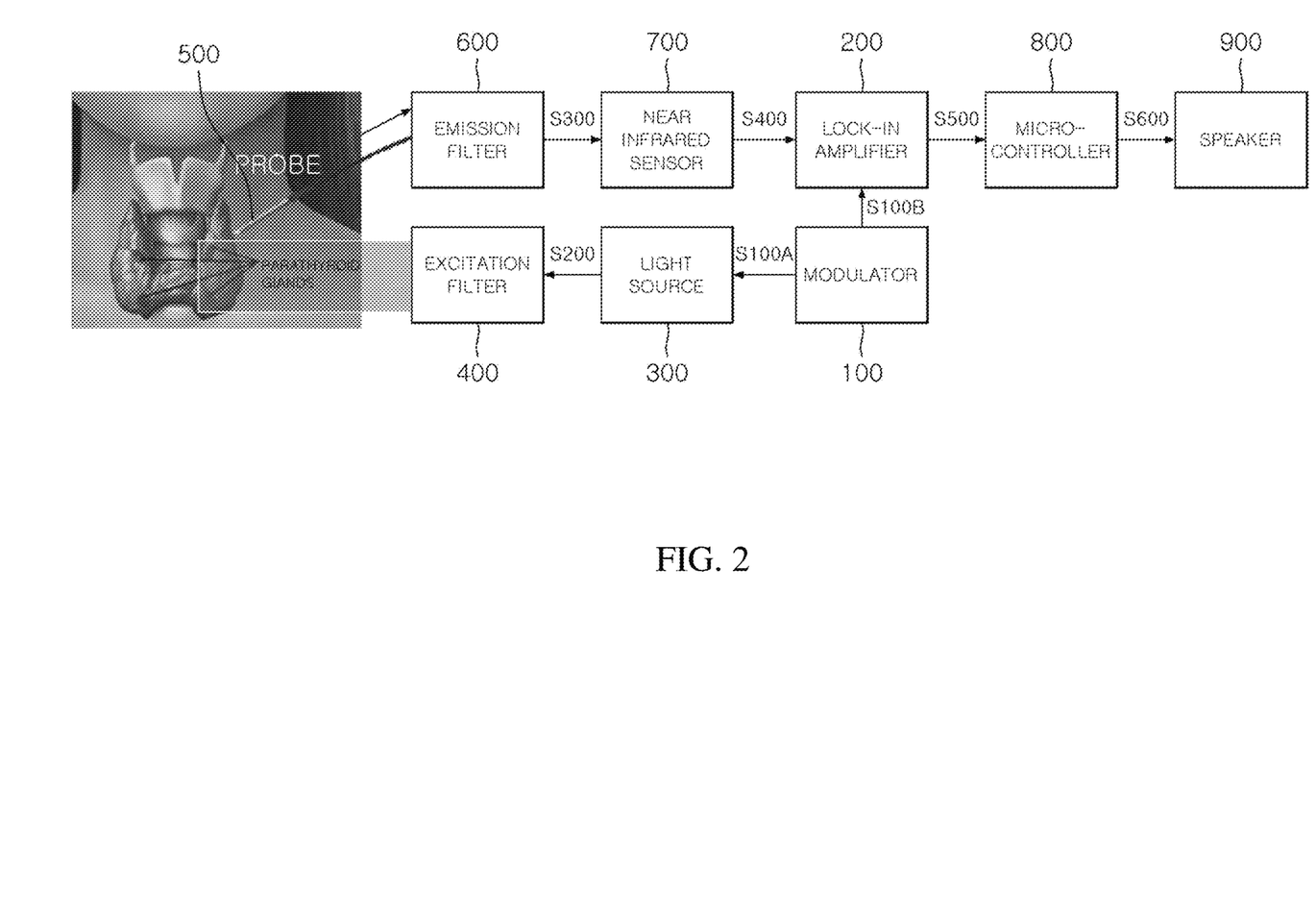
FIG. 2 illustrates a parathyroid sensing system according to an embodiment of the present invention.

FIG. 2 is a diagram illustrating a parathyroid sensing system according to an embodiment of the present invention.

During thyroid surgery, a surgeon first dissects only skin and then images an entire surgical field and the location of the parathyroid in a context thereof and roughly determines the entire surgical field and the location of the parathyroid. Thereafter, thyroid tumors and lymph glands are removed and here, when the location of the parathyroid is determined, a very thin probe which is as large as the size of the parathyroid is used.

The present invention relates to a parathyroid sensing system that sounds an alarm in real time when a surgeon approaches a probe or surgical instrument near the parathyroid gland during surgery.

Since the parathyroid has a particular excitation spectrum and a particular emission spectrum, there should be a light source and a sensing system suitable therefor. In this case, since the excitation spectrum and the emission spectrum generally overlap with each other, an excitation filter and an emission filter should be used.

The parathyroid sensing system according to the present invention includes: a modulator 100 for generating a modulation signal having a predetermined frequency; a lock-in amplifier 200 and a light source 300 which receive information on the modulation signal; and excitation filter 400 for transmitting, among light emitted from the light source, only excitation light that excites the parathyroid glands; a probe 500 and an emission filter 600 connected to the probe 500 and selectively transmitting only autofluorescence emitted from the parathyroid glands; a near-infrared sensor 700 for sensing the autofluorescence that has passed through the emission filter 600, and converting the sensed autofluorescence into an electric signal; and a speaker 900 for generating an alarm through the electric signal. Further, the parathyroid sensing system may further include a micro-controller 800 which converts the electric signal into an electric signal which may be recognized by the speaker.

In the present invention, a heterodyne detection technique is introduced so that parathyroid autofluorescence may be more clearly sensed even in a noise environment such as operating room lighting and electric noise. When the heterodyne detection technique is used, very weak parathyroid autofluorescence may be detected even in a situation in which a fluorescent lamp and a surgical light are turned on during surgery. A process of sensing parathyroid by performing heterodyne detection will be described below.

After a modulation signal at a specific frequency is generated by using the modulator 100, an intensity of a light source is modulated by inputting the modulation signal into a controller of the light source (S100A).

Further, the modulation signal is input into a reference unit of the lock-in amplifier 200 to separate an autofluorescence signal modulated later from a noise environment (S100B).

When the parathyroid is excited through the near-infrared light source 300, autofluorescence modulated at the same frequency is generated in the parathyroid by the modulated light source (S200) and a light signal is sensed by the near-infrared sensor 700 via the emission filter 600 and converted into the electric signal (S300).

When parathyroid autofluorescence is detected by a probe having a very small diameter, an optical fiber is primarily used and since the optical fiber has a unique numerical aperture (NA) (in general, 0.22), only light having a particular angle may be captured. Accordingly, since an amount of light which may be captured is very small, a high-sensitivity near-infrared sensor should be provided in order to detect autofluorescence which is inherently weak in light intensity. In the present invention, a photomultiplier tube (PMT) is used as the high-sensitivity near-infrared sensor 700, but an avalanche photo diode (APD) may also be used. Meanwhile, when a high-sensitivity PMT is used, an exposure time is very short, and as a result, it is possible to sense the parathyroid autofluorescence in real time.

Noise from other lights in the operating room is mixed in the modulated light signal and electric noise is also added via the near-infrared sensor 700. When voltage output from the near-infrared sensor 700 is input into an input unit of the lock-in amplifier 200 (S400), the lock-in amplifier 200 inputs a signal without noise into the micro-controller 800 based on modulation signal information (frequency) of the reference unit previously input from the modulator 100 (S500). The micro-controller 800 converts the signal into the electric signal which may be recognized by the speaker 900 to allow the speaker 900 to generate an alarm sound (S600). The micro-controller 800 may inform whether the parathyroid is detected with a numerical value, a graph, or a color change through a provided output device.

Mode for Invention

Terms or words used in the present specification and claims should not be interpreted as being limited to typical or dictionary meanings, but should be interpreted as having meanings and concepts which comply with the technical spirit of the present disclosure, based on the principle that an inventor can appropriately define the concept of the term to describe his/her own invention in the best manner. Accordingly, configurations illustrated in the exemplary embodiments and drawings disclosed in the present specification are only the most preferred embodiment of the present invention and do not represent all of the technical spirit of the present invention, and thus it is to be understood that various equivalents and modified examples, which may replace the configurations, are possible when filing the present application. Hereinafter, a real-time parathyroid sensing system according to an embodiment of the present invention will be described in detail with reference to the accompanying drawings.

FIG. 2 is a diagram illustrating a parathyroid sensing system according to an embodiment of the present invention.

During thyroid surgery, a surgeon first dissects only skin and then images an entire surgical field and the location of the parathyroid in a context thereof and roughly determines the entire surgical field and the location of the parathyroid. Thereafter, thyroid tumors and lymph glands are removed and here, when the location of the parathyroid is determined, a very thin probe which is as large as the size of the parathyroid is used.

The present invention relates to a parathyroid sensing system that sounds an alarm in real time when a surgeon approaches a probe or surgical instrument near the parathyroid gland during surgery.

Since the parathyroid has a particular excitation spectrum and a particular emission spectrum, there should be a light source and a sensing system suitable therefor. In this case, since the excitation spectrum and the emission spectrum generally overlap with each other, an excitation filter and an emission filter should be used.

The parathyroid sensing system according to the present invention includes: a modulator 100 for generating a modulation signal having a predetermined frequency; a lock-in amplifier 200 and a light source 300 which receive information on the modulation signal; and excitation filter 400 for transmitting, among light emitted from the light source, only excitation light that excites the parathyroid glands; a probe 500 and an emission filter 600 connected to the probe 500 and selectively transmitting only autofluorescence emitted from the parathyroid glands; a near-infrared sensor 700 for sensing the autofluorescence that has passed through the emission filter 600, and converting the sensed autofluorescence into an electric signal; and a speaker 900 for generating an alarm through the electric signal. Further, the parathyroid sensing system may further include a micro-controller 800 which converts the electric signal into an electric signal which may be recognized by the speaker.

In the present invention, a heterodyne detection technique is introduced so that parathyroid autofluorescence may be more clearly sensed even in a noise environment such as operating room lighting, electric noise, etc. When the heterodyne detection technique is used, very weak parathyroid autofluorescence may be detected even in a situation in which a fluorescent lamp and a surgical light are turned on during surgery. A process of sensing parathyroid by performing heterodyne detection will be described below.

After a modulation signal at a specific frequency is generated by using the modulator 100, an intensity of a light source is modulated by inputting the modulation signal into a controller of the light source (S100A).

Further, the modulation signal is input into a reference unit of the lock-in amplifier 200 to separate an autofluorescence signal modulated later from a noise environment (S100B).

When the parathyroid is excited through the near-infrared light source 300, autofluorescence modulated at the same frequency is generated in the parathyroid by the modulated light source (S200) and a light signal is sensed by the near-infrared sensor 700 via the emission filter 600 and converted into the electric signal (S300).

When parathyroid autofluorescence is detected by a probe having a very small diameter, an optical fiber is primarily used and since the optical fiber has a unique numerical aperture (NA) (in general, 0.22), only light having a particular angle may be captured. Accordingly, since an amount of light which may be captured is very small, a high-sensitivity near-infrared sensor should be provided in order to detect autofluorescence which is inherently weak in light intensity. In the present invention, a photomultiplier tube (PMT) is used as the high-sensitivity near-infrared sensor 700, but an avalanche photo diode (APD) may also be used. Meanwhile, when a high-sensitivity PMT is used, an exposure time is very short, and as a result, it is possible to sense the parathyroid autofluorescence in real time.

Noise from other lights in the operating room is mixed in the modulated light signal and electric noise is also added via the near-infrared sensor 700. When voltage output from the near-infrared sensor 700 is input into an input unit of the lock-in amplifier 200 (S400), the lock-in amplifier 200 inputs a signal without noise into the micro-controller 800 based on modulation signal information (frequency) of the reference unit previously input from the modulator 100 (S500). The micro-controller 800 converts the signal into the electric signal which may be recognized by the speaker 900 to allow the speaker 900 to generate an alarm sound (S600). The micro-controller 800 may inform whether the parathyroid is detected with a numerical value, a graph, or a color change through a provided output device.

Figure 3:
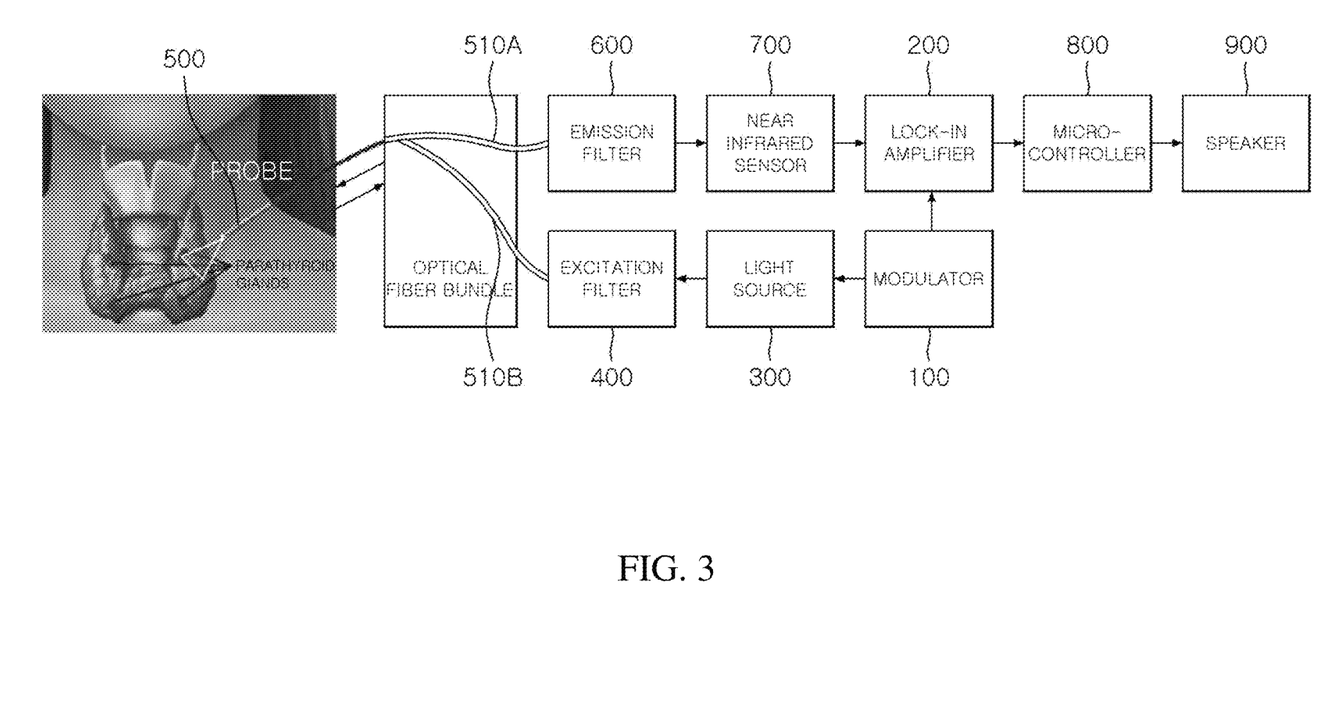
FIG. 3 illustrates a parathyroid sensing system according to another embodiment of the present invention.

FIG. 3 illustrates a parathyroid sensing system according to another embodiment of the present invention.

FIG. 2 illustrates a structure in which the probe and a light source (excitation) are separated, but the embodiment illustrated in FIG. 3 has a structure in which the emission filter 600 is connected to a first optical fiber and the excitation filter 400 is connected to a second optical fiber and both are integrated in one probe.

In the structure illustrated in FIG. 2, since excitation light may be illuminated to a wide area as parallel light, an influence may be removed, in which the intensity of the autofluorescence is changed while the intensity of the excitation light varies depending on a distance between the light source and the parathyroid. In this case, a signal is detected in inverse proportion only to the square of the distance between the probe and the parathyroid gland.

On the contrary, FIG. 3 illustrates a structure in which the excitation light and emission light travel in opposite directions within one probe 500. In the structure, there is an advantage in that the excitation light may be strongly focused and sent to the probe 500. Further, since the probe 500 supplies the excitation light to the parathyroid and also receives the autofluorescence which is emitted, the excitation is illuminated in inverse proportion to the square of the distance and the intensity of the light detected is also in inverse proportion to the square of the distance. Accordingly, when the distance between the probe 500 and the parathyroid decreases, a detected signal rapidly increases.

In the parathyroid sensing system illustrated in FIG. 2, the surgeon should additionally hold an excitation illumination in addition to the probe held in a hand thereof or fix the excitation illumination to the top of a surgical field, but in the parathyroid sensing system illustrated in FIG. 3, since the excitation illumination (light source) is included in the probe 500, a case where the illumination is obscured by other structures, the light is misdirected to areas other than a parathyroid portion, or both hands of the surgeon should be used may be excluded.

Meanwhile, as illustrated in FIG. 3, an optical fiber sending the light and an optical fiber receiving the light may be separated from the beginning by using two or more optical fiber bundles, but a 2×1 beam splitter, an optical circulator, and/or a double cladding fiber which sends and receives the light in each of core and cladding modes may be used, in order to use only one optical fiber.

Figure 4:
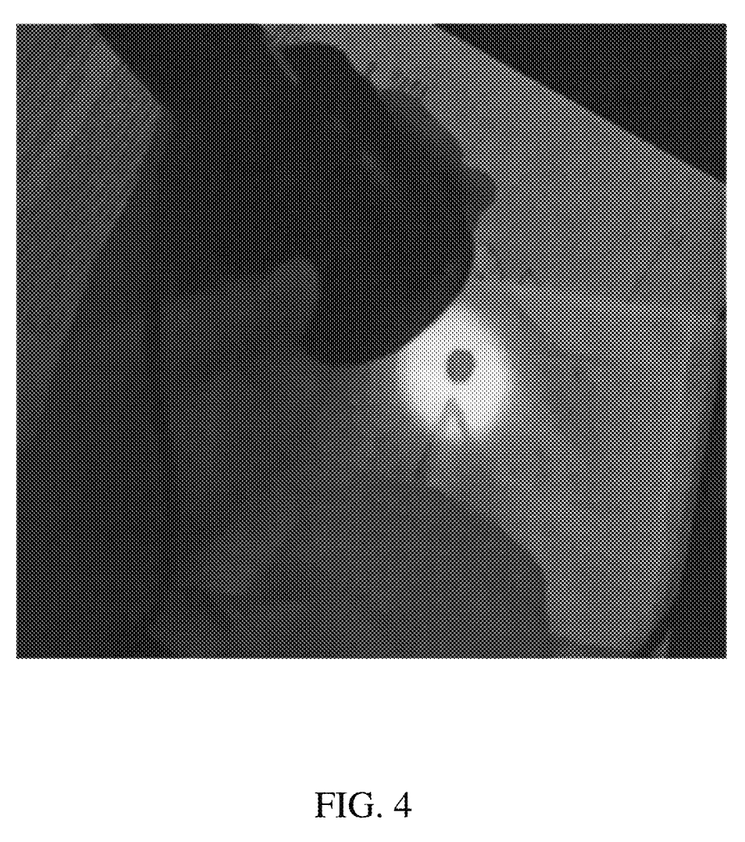
FIG. 4 is a photograph of sensing parathyroid by using a parathyroid sensing system according to the present invention.
Figure 5:
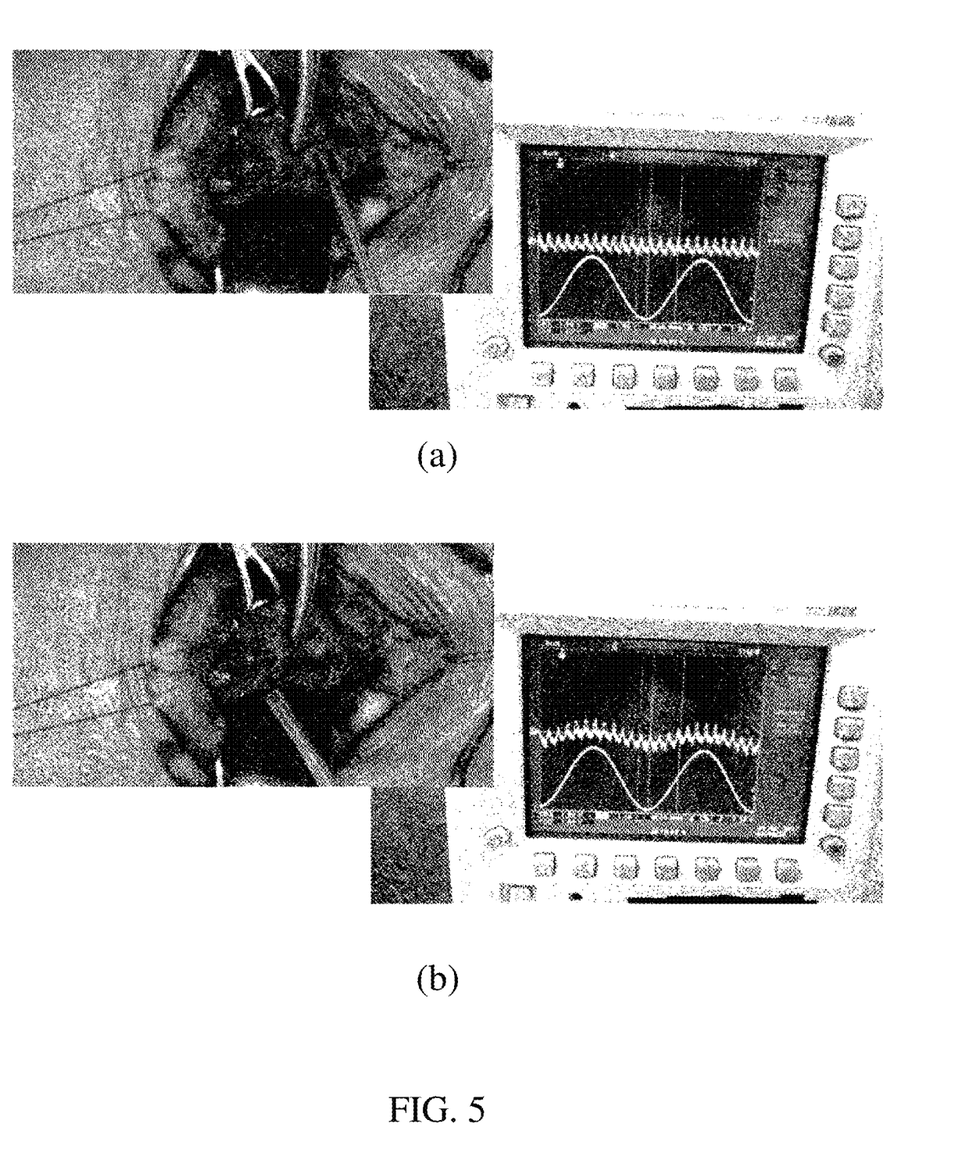
FIG. 5 illustrates observation of a waveform changed by applying a parathyroid sensing system according to the present invention to a part considered as a place where parathyroid is positioned.

FIG. 4 is a photograph of sensing parathyroid by using a parathyroid sensing system according to the present invention and FIG. 5 illustrates observation of a waveform changed by applying a parathyroid sensing system according to the present invention to a part considered as a place where parathyroid is positioned.

FIG. 4 is a photograph of an experiment by the parathyroid sensing system illustrated in FIG. 2, and FIG. 5 is a photograph of an experiment by the parathyroid sensing system illustrated in FIG. 3. Referring to FIGS. 5(a) and 5(b), when the probe approaches a portion where the parathyroid is positioned (FIG. 5(b)), it can be seen that a waveform is rapidly changed, compared to that before (FIG. 5(a)). In the present invention, the corresponding locations may be precisely detected, even when the probe is not directly in contact with the parathyroid glands, by using the autofluorescence characteristics of the parathyroid glands.

Figure 6:
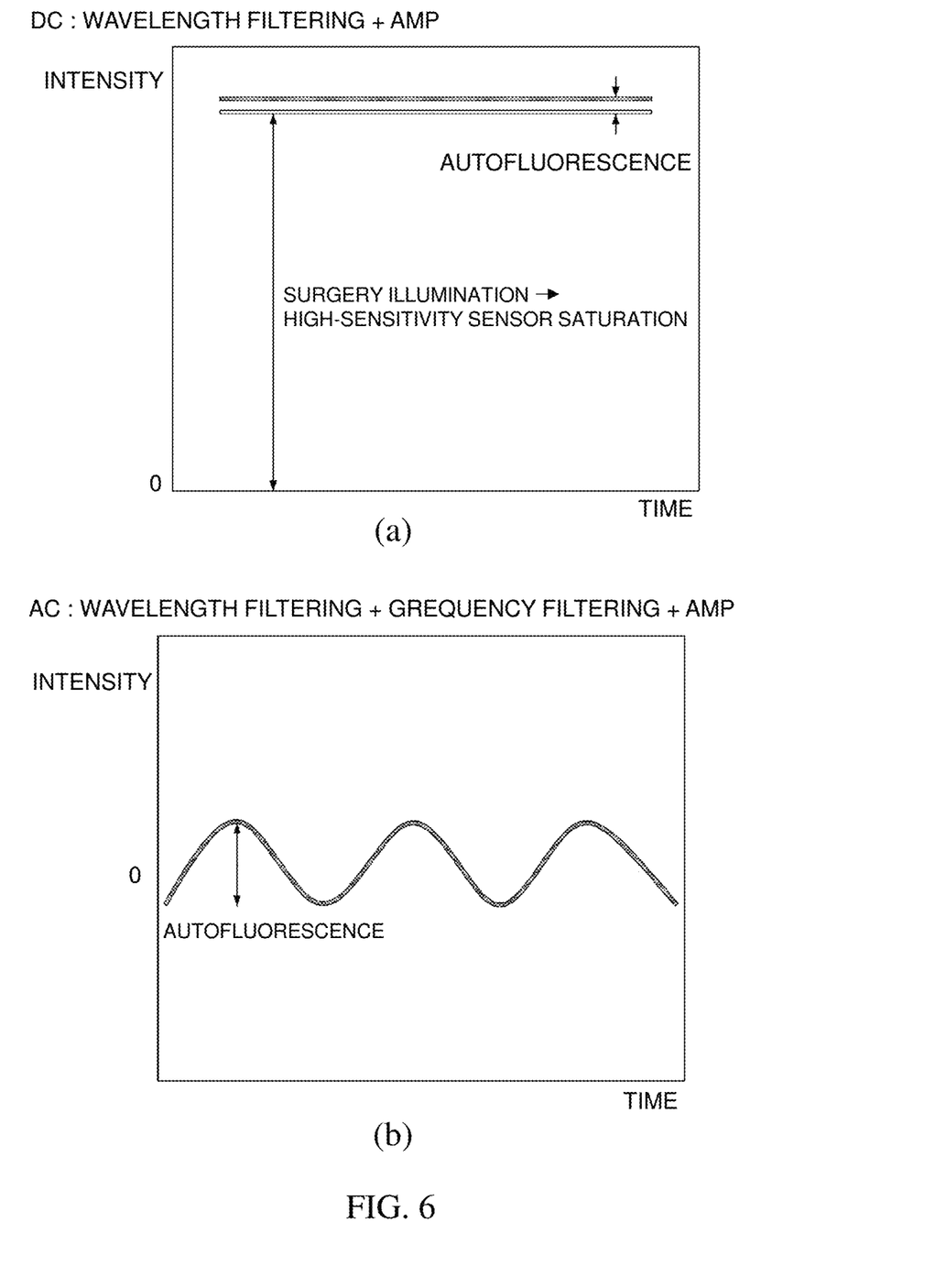
FIG. 6(a) is a graph showing an intensity depending on a time when applying wavelength filtering.
FIG. 6(b) is a graph showing an intensity depending on the time when applying frequency filtering in addition to the wavelength filtering.

FIG. 6(a) is a graph showing an intensity depending on a time when applying wavelength filtering using an optical filter and FIG. 6(b) is a graph showing an intensity depending on the time when applying frequency filtering using modulation in addition to the wavelength filtering.

Compared to performing only the wavelength filtering of dividing the channel (FIG. 6(a)), in the present invention, the frequency filtering is additionally performed in order to use the heterodyne detection technique (FIG. 6(b)). In this case, it can be seen that only the autofluorescence may be selectively measured even in an optical and/or electric noise environment. This means that the autofluorescence exciting the parathyroid is more clearly detected.

Although representative exemplary embodiments of the present invention have been described in detail hereinabove, it will be appreciated by those skilled in the art that various modifications of the exemplary embodiment of the present invention can be made within a limit without departing from the scope of the present invention. Therefore, the scope of the present invention should not be limited to the embodiments and should be defined by the appended claims and equivalents to the appended claims.

What is claimed is:

1. A parathyroid sensing system comprising:
   a modulator for generating a modulation signal having a predetermined frequency;
   a lock-in amplifier and a light source which receive information on the modulation signal;
   an excitation filter for transmitting, among light emitted from the light source, only excitation light that excites parathyroid glands;
   an emission filter connected to a probe and selectively transmitting only fluorescence emitted from the parathyroid glands;
   a near-infrared sensor for sensing the autofluorescence that has passed through the emission filter, and converting the sensed autofluorescence into an electric signal; and
   a speaker for generating an alarm through the electric signal,
   wherein said parathyroid sensing system senses said parathyroid glands based on wavelength filtering and frequency filtering.

2. The parathyroid sensing system of claim 1, wherein the light source includes a controller modulating an intensity of the light source based on the received modulation signal information.

3. The parathyroid sensing system of claim 1, wherein the near-infrared sensor is a PMT or APD.

4. The parathyroid sensing system of claim 1, wherein the lock-in amplifier receives the electric signal from the near-infrared sensor and generates a signal without noise based on the modulation signal information received from the modulator.

5. The parathyroid sensing system of claim 1, further comprising:
   a micro-controller converting the electric signal into an electric signal which may be recognized by the speaker.

6. The parathyroid sensing system of claim 1, wherein the emission filter is connected to a first optical fiber and the excitation filter is connected to a second optical fiber and both are integrated in one probe.

* * * * *

UNITED STATES PATENT AND TRADEMARK OFFICE
CERTIFICATE OF CORRECTION

PATENT NO. : 11,559,248 B2
APPLICATION NO. : 16/764488
DATED : January 24, 2023
INVENTOR(S) : Yeh-Chan Ahn and Sung Chul Bae It is certified that error appears in the above-identified patent and that said Letters Patent is hereby corrected as shown below:

In the Drawings

Please replace Fig. 6 with Fig. 6 as shown on the attached page.

Signed and Sealed this
Twenty-seventh Day of August, 2024

Katherine Kelly Vidal
*Director of the United States Patent and Trademark Office*